United States Patent [19]

Axelsson

[11] Patent Number: 4,619,661
[45] Date of Patent: Oct. 28, 1986

[54] PROSTHESIS FOOT

[76] Inventor: Robert Axelsson, Hunnerydsvägen 92, S-561 46 Huskvarna, Sweden

[21] Appl. No.: 551,987
[22] PCT Filed: Mar. 3, 1983
[86] PCT No.: PCT/SE83/00070
§ 371 Date: Nov. 3, 1983
§ 102(e) Date: Nov. 3, 1983
[87] PCT Pub. No.: WO83/03050
PCT Pub. Date: Sep. 15, 1983

[30] Foreign Application Priority Data

Mar. 5, 1982 [SE] Sweden .............................. 8201389

[51] Int. Cl.[4] .............................................. A61F 2/66
[52] U.S. Cl. ......................................... 623/55; 623/53
[58] Field of Search ..................... 3/6, 7, 12, 22, 23, 3/24

[56] References Cited

U.S. PATENT DOCUMENTS

| 831,330 | 9/1906 | Doebrich | 3/12 |
| 3,098,239 | 7/1963 | Nader | 3/7 |
| 3,335,428 | 8/1967 | Gajdos | 3/7 |
| 3,501,777 | 3/1970 | Degtyarev et al. | 3/7 |
| 4,328,594 | 5/1982 | Campbell et al. | 3/7 |
| 4,461,045 | 7/1984 | Shorter et al. | 3/30 |

FOREIGN PATENT DOCUMENTS

| 354246 | 6/1922 | Fed. Rep. of Germany . |
| 725400 | 9/1942 | Fed. Rep. of Germany ............... 3/7 |
| 3137684 | 6/1982 | Fed. Rep. of Germany . |
| 2293186 | 8/1976 | France .......................................... 3/7 |
| 443017 | 12/1948 | Italy .............................................. 3/7 |
| 139076 | 2/1953 | Sweden . |
| 738618 | 6/1980 | U.S.S.R. . |

Primary Examiner—Richard J. Apley
Assistant Examiner—David J. Isabella
Attorney, Agent, or Firm—Bacon & Thomas

[57] ABSTRACT

A prosthesis foot (1) comprises a light-weight hollow core (3) which by a combination of shape, material and material thickness forms a system of elastic and rigid areas, so that the core in itself forms a joint system, which can be connected directly to a foot adapter (2) without the mediation of separate elastic or articulated elements. The core or skeleton (3) preferably consists of a plastics material having good resistance to folding ("hinge material"), and it is preferably made by blow molding, injection molding, rotation molding, or the like. The new prosthesis foot has low weight, is easy and inexpensive to manufacture and provides for very good simulation of the possibilities of movement and the pattern of movement of the biological foot during walking.

11 Claims, 3 Drawing Figures

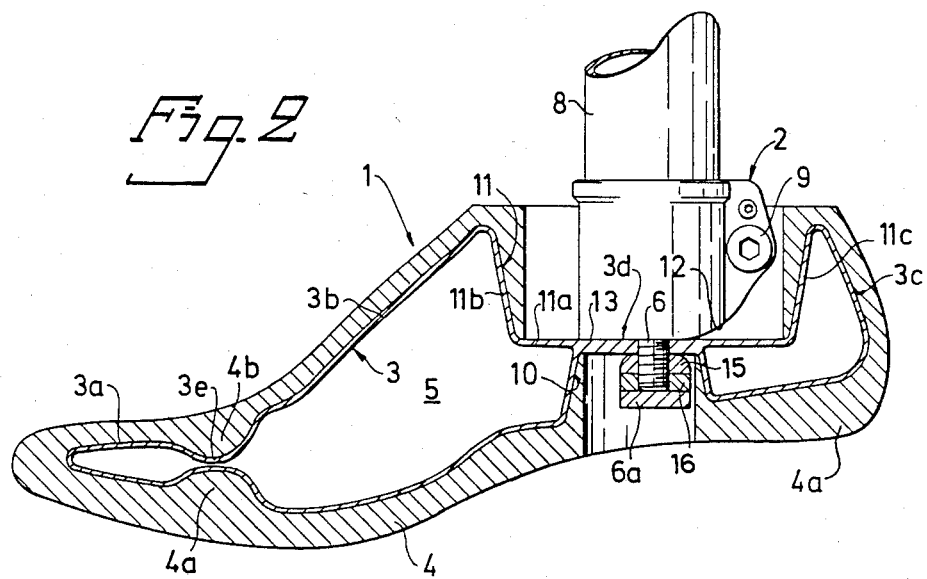
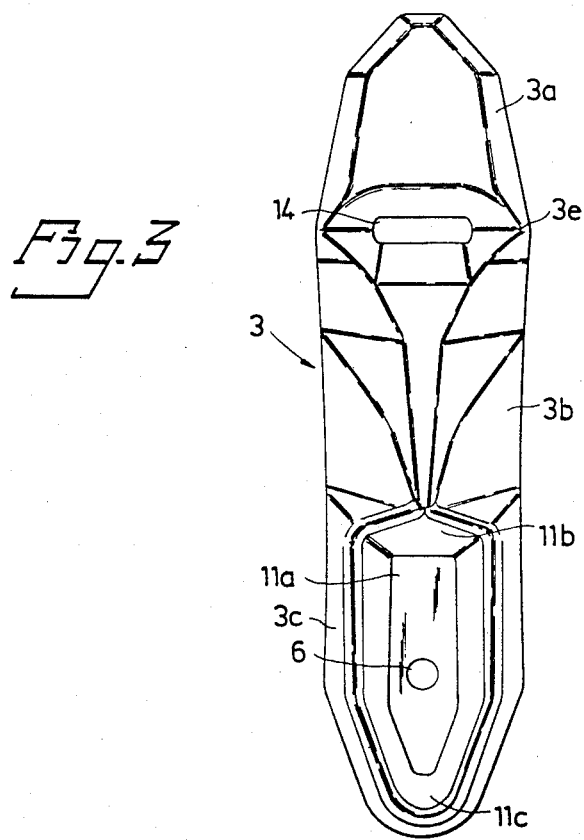

PROSTHESIS FOOT

BACKGROUND OF THE INVENTION

1. Field of the Invention

The present invention relates to a new type of prosthesis foot, i.e. an artificial substitute for a lost biological foot.

2. Description of the Prior Art

The major problem which the invention is intended to solve is to provide a light-weight prosthesis foot which to the greatest possible extent resembles the biological foot concerning possibilities of movement and pattern of movement, effect of forces and loss of energy on walking, shape and appearance, etc., and which is also comparatively easy and cheap to manufacture and can easily be adjusted to different patients.

This problem has proven to be extremely difficult to solve, and although the patent literature comprises an immense number of proposals for solving the problem the presently available prosthesis feet leave much to be desired.

In the most common design of prosthesis feet there is provided a wooden core, to which an adapter for a lower leg prosthesis is attached. In these prosthesis feet separate elastic elements are used for achieving the desired simulation of the joints and the pattern of movement of the biological foot when walking, especially the desired mobility in the ankle joint, the spring joints (e.g. subtalar joint) and the toe area on the heal strike and the push-off. Such constructions, having a comparatively heavy core and separate foot joint mechanisms, are complex and heavy and cause considerable losses of energy on walking (the leg/leg prosthesis forms a long lever with the prosthesis foot at one end thereof). These and other drawbacks would remain even if one would choose a different material than wood as the core material in combination with the separate elastic elements/foot joint mechanisms.

Swedish Pat. No. 139,076 and German Pat. No. 354,246 can be mentioned as examples of prior art prosthesis feet based on a heavy wooden core and having the above mentioned drawbacks. The first mentioned patent disclosed a prostesis foot consisting of a heal and mid-foot portion, which is connected to a toe piece by means of a pair of cooperating plate springs, pressing the toe piece downwards. The heal portion is connected to a lower leg prosthesis in conventional manner by means of a ball joint and a rubber cushion. The latter patent discloses a different type of prosthesis foot—a so-called SACH-foot (Soft Ankle Cushion Heal) prosthesis—wherein a wedge shaped wooden lower leg prosthesis is connected to the prosthesis foot between a wooden toe and mid-foot piece and a heal cushion of rubber, a plate spring being connected between the front foot portion and the rear part of the lower leg prosthesis for providing resilient resistance to downwards/backwards motion of the lower leg prosthesis.

Russian Pat. No. 738,618 discloses an artifical foot comprising a moulded hollow heal and mid-foot piece, which is hingedly joined to a hollow toe piece. This artifical foot has most complex, heavy and expensive mechanisms for joining the foot to the lower leg prosthesis and providing the desired motions. For example, there are multiple connections between the artificial foot and the leg prosthesis, including a multitude of separate connection elements, such as a talocrural shock absorber with two telescoping sockets, a ball joint, a front shock absorber, double rear shock absorbers, rotation units, etc.

SUMMARY OF THE INVENTION

The present invention thus aims at eliminating, or reducing, these and other drawbacks of known prosthesis feet, and to this end there is according to the invention proposed a new type of prosthesis foot, the characteristic features of which are indicated in the subsequent claims and explained further below.

According to one aspect of the invention the prosthesis foot is characterized by a non-homogenous—or a hollow—core which by e.g. a combination of choice of material, material thickness and shape forms a system of elastic and rigid areas, so that the core in itself forms a joint system, which can be connected directly to a leg prosthesis adapter without mediation of any separate articulated elements. In short, the foot joint mechanisms (elastic elements) and the wooden core (rigid element) of the conventional prosthesis feet are thus replaced by one single, hollow, shaped body having corresponding mechanical properties.

According to another aspect of the invention the hollow core is provided with means for attachment of a foot adapter substantially without the mediation of elastic elements, so that the joint and supporting functions which are desired during the walking cycle are achieved by the substantially direct contact between the rigid foot adapter and the hollow core. The direct contact between the rigid adapter and the hollow core is such that it permits movements in all directions, including lateral movements (pronation and supernation) and rotation movements, however with a limited mobility in the dorsal direction. The prosthesis according to the invention permits a "soft" dorsal stop, thereby avoiding unnecessarily great strain at the stop. As is well known the dorsal stop for a noraml patient occurs when the leg/leg prosthesis has just passed the vertical line.

As already mentioned the indicated properties of the hollow core are primarily determined by the choice of material, the thickness of the material and the shape of the core. The requirements on the material, at least after having being shaped to this core, are primarily that it shall be capable of standing the repeated deformation which the walking movement involves, i.e. have very high resistance to folding ("hinge properties"). Further, it should have good ability of elastic recovery, i.e. a good plastic memory. A great number of plastic materials are available, and the person skilled in the art can easily select a suitable material for each situation, for example a polyolefine such as polypropylene, polyolefin (polypropylene)/rubber mixtures, Hytrel ®, etc.

The hollow core of the prosthesis foot according to the invention can be manufactured by methods which are known per se and which make it possible to provide the desired shape and, if desired, varying material thickness for the prosthesis foot to provide the desired joint and supporting functions during the walking cycle. One suitable such method is blow molding of plastics, and other examples of suitable methods of manufacture are rotation molding, injection molding, etc. As mentioned such methods of manufacture are per se conventional and will therefore not be described further in this context.

These and other characteristics and advantages of the prosthetis foot according to the invention will appear in more detail from the following description of an example of a suitable embodiment with reference to the enclosed drawings.

BRIEF DESCRIPTION OF THE DRAWINGS

FIG. 2 is a view corresponding to FIG. 1 but illustrating an alternative embodiment of the means for attaching the prosthesis to a foot adapter.

FIG. 3 is a schematic top plan view of the hollow core of the prosthesis foot of FIG. 1.

DETAILED DESCRIPTION OF THE PREFERRED EMBODIMENT

Figure 1:
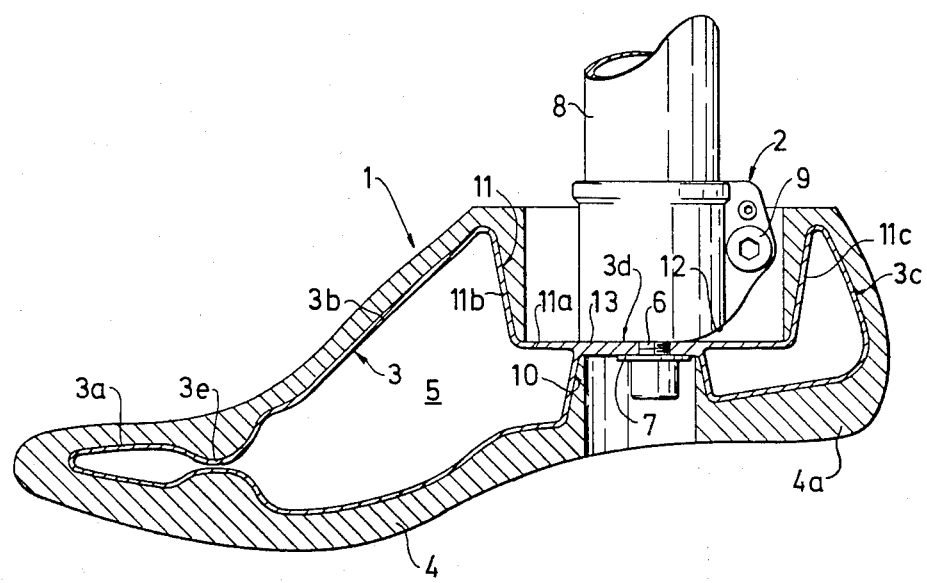
FIG. 1 in schematic longitudinal section illustrates a prosthesis foot according to the invention connected to a foot adapter.

In the drawing the prosthesis foot is generally designated by the reference numeral 1, The foot adapter in general is referenced 2. In the shown embodiment the prosthesis foot 1 essentially consists of a hollow, shaped body or core 3 which is covered by a suitable covering 4, e.g. of polyurethane. As indicated above and will be explained further below the hollow core, or plastic skeleton, 3 together with the foot adapter 2 form the "joint system" of the prosthesis foot. The covering 4 but primarily serves to function as a "foot sole" and for the rest to give the prosthesis foot a cosmetically attractive design.

In the illustrated embodiment the core 3 consists of a comparatively thin plastic shell enclosing an inner cavity 5 which can be open or closed. In the illustrated case the continuous core or skeleton 3 comprises a toe portion 3a, a mid-foot portion 3b, a heal portion 3c and an adapter attachment portion 3d. The transition between the mid-foot portion 3b and the toe or front foot portion 3a is, by means of a recessed portion 3e or otherwise, shaped so that if forms a "joint" corresponding to a toe joint. It is, however, within the scope of the invention to replace the toe portion 3a by any conventional toe joint device.

In the illustrated embodiment the prosthesis foot 1 is attached to the foot adapter 2 by means of a bolt 6, with a washer 7, extending through the attachment portion 3d of the skeleton 3. The adapter 2 is in turn connected to a tubular skeleton part 8 of a lower leg prosthesis or the like (not shown) by means of a suitable fastening device 9. The bolt head 6 is located in a recess 10 provided in the bottom side of the skeleton, whereas the adapter 2 is mounted in a top side recess 11 of the plastic skeleton 3. The recess 11 has an essentially planar bottom 11a with side walls 11b, 11c directed obliquely upwards.

The adapter 2 substantially directly (from the functional viewpoint unessential washers or spacers can be present) contacts the substantially planar bottom 11a of the skeleton 3. The front part of the adapter 13 (i.e. in front of the bolt 6) is substantially planar in its contact with the bottom 11a, whereas its rear part (i.e. behind the bolt 6) can have convex or rounded shape (as at 12, for reasons that will be explained further below).

The function of the prosthesis foot is best explained with reference to the walking cycle heal strike—dorsal stop—toe rolling. The walking cycle is begun by the heal strike against the ground, and the great forces involved therein are absorbed by a thicker heal portion 4a of the sole and the heal portion 3c. On the heal strike it is, however, primarily essential to provide a soft ankle joint, and this is achieved by cooperation between the adapter 2 and the hollow body 3, which, thanks to its shape, absorbs the created forces. The softness in the ankle joint can be controlled further by variation of the curvature of the convex portion 12 on the adapter 2: the smaller the radius the softer the ankle joint.

The walking step is then continued by rolling forwards to the dorsal stop, which takes place in the forward substantially planar contact surface 13 of the foot adapter will contact the skeleton surface 11a. Because of the elasticity of the material in the portion 11a, and in the entire skeleton body 3, the dorsal stop will not be abrupt, but will take place with a certain resilience. Thereafter the toe joint 3e turns into function, and as mentioned above the same can alternatively consist of a conventional toe joint (or simply be left out).

An alternative embodiment of the means for fastening the prosthesis foot 1 to the foot adapter 2 is shown in FIG. 2, wherein like parts as in FIG. 1 have the same reference numerals. In this embodiment two shims or spacers 15 and 16 are provided between the bolt head 6a and the planar bottom 11a of the attachment recess 11. The first spacer 15 has rounded edges on the side facing the bottom 11a, and it is made of a hard material, preferably hard plastics such as nylon. The second spacer 16, which is located between the first spacer 15 and the bolt head (or nut) 6a is made of resilient material, preferably a resilient plastics material such as neoprene. By the combination of spacers 15 and 16 there is obtained an automatic adjustment for cold flow in the core bottom 11a and the spacer 12.

FIG. 3 shows a preferred embodiment of the core 3 viewed from above. As can be seen there is provided a hole 14 in the center portion of the toe joint area 3e. The purpose of this hole is to attach the covering 4 to the core 3 in a manner such that the covering 4 is loosely provided around the core 3, however with interconnection between the covering parts 4a and 4b (FIG. 1) through the hole 14. This interconnection can be achieved by e.g. molding the resilent covering 4 around the core 3 without bonding to the same, said interconnection being formed by the covering material filling the hole 14, thus forming an integral covering including a piece of material joining the covering portions 4a and 4b through the hole 14. It has been found that considerable advantages are obtained on the contacts with the ground during the walking cycle when using this embodiment, wherein the covering 4 is allowed to be displaced somewhat along the core 3 (while still being retained in its general position by the interconnection through the hole 14).

As should have appeared from the above the disclosed design of the prosthesis foot offers, by the combination of a rigid adapter 2 which is connected directly to the disclosed hollow foot body 3, to a great extent "anatomically correct" simulation of the supporting functions as well as the joint functions of a biological foot. Supporting function/relative rigidity is primarily achieved, by the continuous shape of the skeleton 3, and locally at the adapter by the side walls 11b, 11c. The rotation of the adapter 2 around the bolt 6 permits torsional movements.

The invention is, of course, not limited to the embodiment described above and specifically shown in the drawing, but many modifications and variations are possible within the scope of the inventive idea and the subsequent claims. One could, for example, within the scope of the invention, imagine using an adapter 2 which is firmly united with skeleton 3 or forms an integral part of the skeleton 3.

What is claimed is:

1. An artificial foot comprising a flexible and elastic shell of unitary construction having a continuous hollow core, said shell having at least a mid-foot portion, a heel portion, and a recessed portion wherein said shell is formed with predetermined areas of elasticity so that articulation and resiliency of said foot resembles the heel strike, dorsal stop and toe rolling pattern of a natural foot during walking;

said recessed portion is spaced a distance from said sole portion and having a substantially planar bottom portion surrounded by side walls thereby forming substantially a blind bore;

said foot being coupled to a lower leg means through a substantially rigid foot adapter, said adapter being directly connected to said foot in said recessed portion such that the foot adapter contacts said bottom portion without the mediation of any articulating elements such that the joint and supporting function which occur during walking are achieved by substantially direct contact between the foot adapter and recessed portion and the predetermined areas of elasticity of said shell.

2. A prosthesis foot according to claim 1, wherein the recessed portion includes side walls wherein at least one of the side walls diverges obliquely upwards from said bottom.

3. A prosthesis foot according to claim 1, wherein the foot adapter has an essentially planar portion which is substantially rigid and contacts said bottom portion so that the contact between these two portions causes dorsal stop.

4. A prosthesis foot according to claim 1, wherein the foot adapter has a rounded lower rear portion which is arranged to contact said bottom portion of the core so that a soft ankle joint arrangement occurs on the heel strike during walking.

5. A prosthesis foot according to claim 1, wherein said shell comprises a plastic material having high resistance to folding.

6. A prosthesis foot according to claim 1, further comprising a resilient covering which covers said shell on at least its bottom side.

7. A prosthesis foot according to claim 6, wherein the resilient covering encloses at least a major portion of said shell to permit limited sliding motion of the resilient covering relative to said shell upon use in a walking motion.

8. A prosthesis foot according to claim 1, wherein said shell contains an aperture in the center portion of the toe joint area and a portion of the resilient covering passes through the aperture.

9. A prosthesis foot according to claim 8, wherein the portion of the resilient covering which passes through the aperture is integral with a portion of the resilient covering on the opposite side of the aperture.

10. A prosthesis foot according to claim 1, wherein said shell includes a second recessed portion, and the foot adapter is connected to said shell by means of a bolt.

11. A prosthesis foot according to claim 10, wherein the bolt includes a bolthead located in the second recessed portion; a shim located on the bolt between the bolt and said shell, said shim having rounded edges on the side facing said shell.

* * * * *